United States Patent [19]
Woudenberg et al.

[11] Patent Number: 6,015,674
[45] Date of Patent: Jan. 18, 2000

[54] APPARATUS AND METHOD FOR DETECTING NUCLEIC ACID AMPLIFICATION PRODUCTS

[75] Inventors: Timothy M. Woudenberg, Moss Beach; Kevin S. Bodner, San Mateo; Charles R. Connell, Redwood City; John Shigeura, Fremont, all of Calif.; David H. Tracy, Norwalk; Eugene F. Young, Wilton, both of Conn.

[73] Assignee: Perkin-Elmer Corporation Applied Biosystems Division, Foster City, Calif.

[21] Appl. No.: 09/046,114

[22] Filed: Mar. 20, 1998

Related U.S. Application Data

[63] Continuation of application No. 08/752,973, Dec. 2, 1996, Pat. No. 5,928,907, which is a continuation of application No. 08/235,411, Apr. 29, 1994, abandoned.

[51] Int. Cl.$^7$ ............................... C12Q 1/68; C12P 19/34
[52] U.S. Cl. ......................... 435/6; 435/91.2; 422/82.05; 422/82.08; 422/82.09
[58] Field of Search .................. 435/6, 91.2; 422/82.05, 422/82.08, 82.09

[56] References Cited

U.S. PATENT DOCUMENTS

| | | | |
|---|---|---|---|
| 4,150,295 | 4/1979 | Wieder | 250/458 |
| 4,954,435 | 9/1990 | Krauth | 435/7 |
| 5,135,717 | 8/1992 | Renzoni et al. | 422/61 |
| 5,538,848 | 7/1996 | Livak et al. | 435/5 |
| 5,547,861 | 8/1996 | Nadeau et al. | 435/91.2 |
| 5,556,751 | 9/1996 | Stefano | 435/6 |
| 5,585,242 | 12/1996 | Bouma et al. | 435/6 |
| 5,593,867 | 1/1997 | Walker et al. | 435/91.2 |

FOREIGN PATENT DOCUMENTS

| | | | |
|---|---|---|---|
| 0 421 156 A2 | 10/1991 | European Pat. Off. | G01N 21/64 |
| 0 512 334 A2 | 11/1992 | European Pat. Off. | C12Q 1/68 |

OTHER PUBLICATIONS

Lee, L. et al., "Allelic discrimination by nick–translation PCR with fluorogenic probes", Nucleic Acids Research, vol. 21, No. 16, pp. 3761–3766 (1993).

Higuchi, R. et al., "Simultaneous Amplification and Detection of Specific DNA Sequences", Bio–Technology, vol. 10, Apr. 1992, pp. 413–417.

Gershoni, J. et al., "The Use of an Internal Standard for Semiquantitative Analysis of Low Temperature (77K) Fluorescence of Photosyntheic Cells", Analytical Biochemistry, vol. 104, pp. 315–320, (1980).

Krause, G. et al., "Characterization of Chlorophyll Fluorescence Quenching in Chloroplasts by Fluorescence Spectroscopy at 77K", Biochimica et Biophysica Acta., vol. 723, pp. 169–175 (1983).

*Primary Examiner*—Kenneth R. Horlick
*Attorney, Agent, or Firm*—David J. Weitz; Wilson Sonsini Goodrich & Rosati

[57] ABSTRACT

An apparatus is provided which includes a sample holder for holding a reaction chamber which includes an optical interface, a fiber optic cable for delivering an excitation beam to a sample housed within the reaction chamber and for receiving light emitted by the sample, and a lens co-axially disposed with the fiber optic cable and positioned outside the reaction chamber for focusing the excitation beam through the optical interface and within a volume of the sample and for collecting and transmitting to the fiber optic cable light emitted within the volume of the sample.

32 Claims, 6 Drawing Sheets

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 25 nucleotides
      (B) TYPE: nucleic acid
      (C) STRANDEDNESS: single
      (D) TOPOLOGY: linear    (xi) SEQUENCE DESCRIPTION: SEQ ID NO: 1:

TCACCCACAC TGTGCCCATC TACGA       25

(2) INFORMATION FOR SEQ ID NO: 2:

(i) SEQUENCE CHARACTERISTICS:
      (A) LENGTH: 26 nucleotides
      (B) TYPE: nucleic acid
      (C) STRANDEDNESS: single
      (D) TOPOLOGY: linear    (xi) SEQUENCE DESCRIPTION: SEQ ID NO: 2:

CAGCGGAACC GCTCATTGCC AATGGT       26

(2) INFORMATION FOR SEQ ID NO: 3:

(i) SEQUENCE CHARACTERISTICS:
      (A) LENGTH: 26 nucleotides
      (B) TYPE: nucleic acid
      (C) STRANDEDNESS: single
      (D) TOPOLOGY: linear    (xi) SEQUENCE DESCRIPTION: SEQ ID NO: 3:

ATGCCCTCCC CCATGCCATC CTGCGT       26

APPARATUS AND METHOD FOR DETECTING NUCLEIC ACID AMPLIFICATION PRODUCTS

RELATIONSHIP TO COPENDING APPLICATIONS

This application is a continuation of U.S. application Ser. No. 08/752,973, filed Dec. 2, 1996, U.S. Pat. No. 5,928,907, which is a continuation of U.S. application Ser. No. 08/235,411, filed Apr. 29, 1994, abandoned, both of which are incorporated herein by reference in their entirety.

FIELD OF THE INVENTION

The invention relates generally to the field of nucleic acid amplification, and more particularly to a system for measuring in real time polynucleotide products from nucleic acid amplification processes, such as polymerase chain reaction (PCR).

BACKGROUND

Nucleic acid sequence analysis is becoming increasingly important in many research, medical, and industrial fields, e.g. Caskey, Science 236: 1223–1228 (1987); Landegren et al, Science, 242: 229–237 (1988); and Arnheim et al, Ann. Rev. Biochem., 61: 131–156 (1992). The development of several nucleic acid amplification schemes has played a critical role in this trend, e.g. polymerase chain reaction (PCR), Innis et al, editors, PCR Protocols (Academic Press, New York, 1990); McPherson et al, editors, PCR: A Practical Approach (IRL Press, Oxford, 1991); ligation-based amplification techniques, Barany, PCR Methods and Applications 1: 5–16 (1991); and the like.

PCR in particular has become a research tool of major importance with applications in cloning, analysis of genetic expression, DNA sequencing, genetic mapping, drug discovery, and the like, e.g. Arnheim et al (cited above); Gilliland et al, Proc. Natl. Acad. Sci., 87: 2725–2729 (1990); Bevan et al, PCR Methods and Applications, 1: 222–228 (1992); Green et al, PCR Methods and Applications, 1: 77–90 1991); Blackwell et al, Science, 250: 1104–1110 (1990).

A wide variety of instrumentation has been developed for carrying out nucleic acid amplifications, particularly PCR, e.g. Johnson et al, U.S. Pat. No. 5,038,852 (computer-controlled thermal cycler); Wittwer et al, Nucleic Acids Research, 17: 4353–4357 (1989)(capillary tube PCR); Hallsby, U.S. Pat. No. 5,187,084 (air-based temperature control); Garner et al, Biotechniques, 14: 112–115 (1993) (high-throughput PCR in 864-well plates); Wilding et al, International application No. PCT/US93/04039 (PCR in micro-machined structures); Schnipelsky et al, European patent application No. 90301061.9 (publ. No. 0381501 A2)(disposable, single use PCR device), and the like. Important design goals fundamental to PCR instrument development have included fine temperature control, minimization of sample-to-sample variability in multi-sample thermal cycling, automation of pre- and post-PCR processing steps, high speed cycling, minimization of sample volumes, real time measurement of amplification products, minimization of cross-contamination, or sample carryover, and the like. In particular, the design of instruments that permit PCR to be carried out in closed reaction chambers and monitored in real time is highly desirable. Closed reaction chambers are desirable for preventing cross-contamination, e.g. Higuchi et al, Biotechnology, 10: 413–417 (1992) and 11: 1026–1030 (1993); and Holland et al, Proc. Natl. Acad. Sci., 88: 7276–7280 (1991). Clearly, the successful realization of such a design goal would be especially desirable in the analysis of diagnostic samples, where a high frequency of false positives and false negatives would severely reduce the value of the PCR-based procedure. Real time monitoring of a PCR permits far more accurate quantitation of starting target DNA concentrations in multiple-target amplifications, as the relative values of close concentrations can be resolved by taking into account the history of the relative concentration values during the PCR. Real time monitoring also permits the efficiency of the PCR to be evaluated, which can indicate whether PCR inhibitors are present in a sample.

Holland et al (cited above) and others have proposed fluorescence-based approaches to provide real time measurements of amplification products during a PCR. Such approaches have either employed intercalating dyes (such as ethidium bromide) to indicate the amount of double stranded DNA present, or they have employed probes containing fluorescer-quencher pairs (the so-called "Tac-Man" approach) that are cleaved during amplification to release a fluorescent product whose concentration is proportional to the amount of double stranded DNA present.

Unfortunately, successful implementation of these approaches has been impeded because the required fluorescent measurements must be made against a very high fluorescent background. Thus, even minor sources of instrumental noise, such as the formation of condensation in the chamber during heating and cooling cycles, formation of bubbles in an optical path, particles or debris in solution, differences in sample volumes—and hence, differences in signal emission and absorbence, and the like, have hampered the reliable measurement of the fluorescent signals.

In view of the above, it would be advantageous if an apparatus were available which permitted stable and reliable real time measurement of fluorescent indicators of amplification products resulting from any of the available nucleic acid amplification schemes.

SUMMARY OF THE INVENTION

The invention relates to a system for carrying out real time fluorescence-based measurements of nucleic acid amplification products. In a preferred embodiment of the invention, an excitation beam is focused into a reaction mixture containing (i) a first fluorescent indicator capable of generating a first fluorescent signal whose intensity is proportional to the amount of an amplification product in the volume of the reaction mixture illuminated by the excitation beam and (ii) a second fluorescent indicator homogeneously distributed throughout the reaction mixture and capable of generating a second fluorescent signal proportional to the volume of reaction mixture illuminated by the excitation beam. It is understood that the proportionality of the fluorescent intensities is for a constant set of parameters such as temperature, pH, salt concentration, and the like, that independently influence the fluorescent emissions of organic dyes.

Preferably, the excitation beam is focused into the reaction mixture by a lens through a portion of a wall of a closed reaction chamber containing the reaction mixture. In further preference, the same lens collects the first and second fluorescent signals generated by the first and second fluorescent indicators, respectively, in response to the excitation beam; thus, variability in the collected signal due to misalignment of excitation and collection optics is avoided. In this embodiment, whenever the lens directs the excitation beam through a portion of a wall of the closed reaction chamber which is not in contact with the reaction mixture, that portion of the wall is heated so that condensation from the reaction mixture does not form in the optical pathway of the fluorescent signals being collected by the lens, thereby removing another source of variability in the collected signal.

In the most preferred embodiment, the reaction chamber is a tube with a closed end, referred to herein as the bottom of the tube, and an open end, referred to herein as the top of the tube, which can be closed with a cap such that a leak-proof seal is formed. In other words, once a reaction mixture is placed in the tube and the cap is attached a closed reaction chamber is formed. In this most preferred embodiment, (1) the reaction mixture fills a portion of the tube, generally at the bottom of the tube, such that a void is left between the cap of the tube and a top surface of the reaction mixture, and (2) the lens without contacting the cap focuses the excitation beam through the cap into the reaction mixture through its top surface and collects the resulting fluorescence generated by the first and second fluorescent indicators. As mentioned above, the portion of the tube through which the excitation beam passes—the cap in this embodiment—is heated to prevent the formation of condensation which would introduce an added source of variability in the measurement of the collected fluorescent signals. Potential variability that could arise from sequential analysis of the first and second fluorescent signals is eliminated by simultaneously analyzing the signals by spectrally separating the signal light onto an array of photo detectors, e.g. by diffracting the signal onto a charged-coupled device (CCD) array.

As discussed more fully below, an excitation beam generated by a single light source, e.g. a laser, is conveniently distributed to a plurality of closed reaction chambers by fiber optics. Likewise, the same fiber optics can collect the fluorescent signals from the plurality of reaction chambers for analysis by a single detection and analysis system.

Preferably, the system is employed with the PCR amplification of nucleic acids.

The system of the invention permits accurate real time monitoring of nucleic amplification reactions by providing apparatus and fluorescent reagents for generating a stable fluorescent signal proportional to the amount of amplification product and independent of variations in the volume of reaction mixture. The availability of data showing the progress of amplification reactions leads to more accurate estimates of relative starting concentrations of target nucleic acids, to rapid assessment of the efficiency of the amplification reactions, and opens the possibility of reduced reagent usage and feedback reaction control.

DEFINITIONS

As used herein, the term "stable" in reference to a fluorescent signal means that the root means square (RMS) deviation in the signal due to noise is less than or equal to two percent of the average signal magnitude. More preferably, stable means that the RMS deviation in the signal due to noise is less than or equal to one percent of the average signal magnitude.

DETAILED DESCRIPTION OF THE INVENTION

The invention is a fluorescence-based system for monitoring in real time the progress of a nucleic acid amplification reaction. The type of amplification scheme used with the system is not critical, but generally the system requires either the use of a nucleic acid polymerase with exonuclease activity or a population of double stranded DNA which increases during the course of the reaction being monitored. Exemplary amplification schemes that may be employed with the system of the invention include PCR, ligase-based amplification schemes, such as ligase chain reaction (LCR), Q-beta replicase-based amplification schemes, strand displacement amplification (SDA) schemes, such as described by Walker et al, Nucleic Acids Research, 20: 1691–1696 (1992), and the like. A comprehensive description of nucleic acid amplification schemes is provided by Keller and Manak, DNA Probes, Second Edition (Stockton Press, New York, 1993). Fundamental to the system is the measurement of ratios of fluorescent intensities of a first fluorescent indicator and an internal standard, referred to herein as a second fluorescent indicator. The first and second fluorescent indicators must be spectrally resolvable. That is, their respective emission spectra must be sufficiently non-overlapping so that separate emission peaks are observed in the combined spectrum. Clearly, the system may be generalized to include a plurality of first fluorescent indicators, e.g. to monitor the simultaneous amplification of several target nucleic acids in a single reaction, so that a plurality of fluorescent intensity ratios are monitored. Several spectrally resolvable dyes suitable for use in such embodiments are disclosed in Fung et al, U.S. Pat. No. 4,855,225; Menchen et al, U.S. Pat. No. 5,188,934; Bergot et al, International Application PCT/US90/05565; and like references.

The system includes a sample interface—that is, optical components operationally associated with a closed reaction chamber—which comprises a lens for focusing an excitation beam into the reaction mixture and for collecting the resulting fluorescence and a fiber optic for transmitting both the excitation beam from a light source to the lens and the fluorescent signals from the lens to a detection and analysis means. Preferably, the reaction mixture is contained in a closed reaction chamber to prevent cross-sample contamination, or so-called "carryover." The lens therefore focuses the excitation beam and collects fluorescence through a portion of a wall of the closed reaction chamber.

Figure 1:
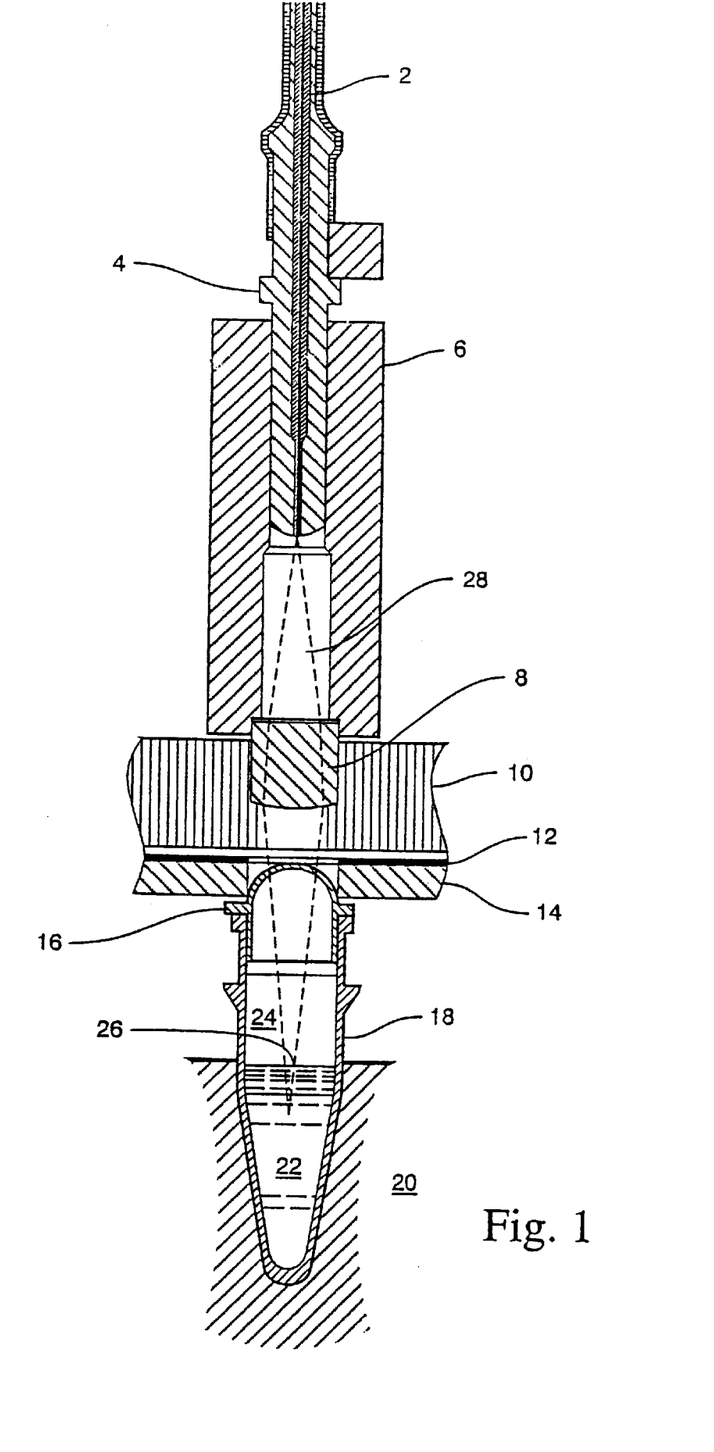
FIG. 1 diagrammatically illustrates a preferred embodiment of the sample interface components of the system of the invention.

As mentioned above, the preferred reaction chamber is a tube, e.g. having the geometry and volume of a conventional Eppendorf tube. The tube is closed after the reaction mixture is added by attaching a cap to the open end of the tube. In a preferred embodiment of the sample interface for PCR, the lens directs the excitation beam and collects fluorescence through the cap of the tube, as illustrated in FIG. 1. In the illustrated configuration, a first end fiber optic 2 is held by ferrule 4, housing 6, and plate 10 in a co-axial orientation with lens 8. A second end of fiber optic 2 (not shown) is operationally associated with a light source and detection and analysis means, discussed more fully below. The distance between the end face of fiber optic 2 and lens 8 is determined by several factors, including the numerical aperture of the fiber optic, the geometry of tube 18, the focal length of lens 8, the diameter of lens 8, and the like. Guidance for selecting values for such variables in any particular embodiment is readily found in standard texts on optical design, e.g. Optics Guide 5 (Melles Griot, Irvine, Calif., 1990), or like reference. In the illustrated embodiment, lens 8 has a diameter of 8 mm and is composed of material BK7, available from Edmund Scientific (Barrington, N.J.). Fiber optic 2 has a numerical aperture of 0.2. Preferably, the design permits maximal transmission of excitation beam 28 to reaction mixture 22. For example, lens 8, numerical aperture of fiber optic 2, and the distance between the end of fiber optic 2 and lens 8 are selected so that the diameter of lens 8 equals or exceeds the diameter of excitation beam 28 where beam 28 impinges on the lens (as illustrated in FIG. 1). Excitation beam 28 is focused through cap 16, void 24, and top surface 26 of reaction mixture 22 to a region approximately 1–3 times the diameter of the fiber optic just below, e.g. 1–3 mm, surface 26. This degree of focusing is not a critical feature of the embodiment; it is a consequence of adapting the sample interface to the geometry and dimensions of a sample holder of a commercially available thermal cycler. In other embodiments, the geometry and dimension may permit a sharper focus into the reaction mixture.

The lens of the invention may have a variety of shapes depending on particular embodiments. For example, the lens may be a sphere, truncated sphere, cylinder, truncated cylinder, oblate spheroid, or truncated oblate spheroid, or the like, and may be composed of any suitably transparent refractive material, such as disclosed by Hlousek, U.S. Pat. No. 5,037,199; Hoppe et al, U.S. Pat. No. 4,747,87; Moring et al, U.S. Pat. No. 5,239,360; Hirschfield, U.S. Pat. No. 4,577,109; or like references.

Fluorescent light generated by excitation beam 28 is collected by lens 8 along approximately the same optical pathway as that defined by excitation beam 28 and focused onto the end of fiber optic 2 for transmission to optical separation and analysis components of the system.

In further preference, the sample interface also includes means for heating the portion of the wall of the reaction chamber used for optical transmission in order to reduce variability due to scatter and/or absorption of the excitation beam and signal from condensation of reaction mixture components. In the embodiment of FIG. 1, the portion of the reaction chamber (tube 18) wall used for optical transmission is cap 16. Accordingly, heating element 12 and heat-conductive platen 14 are employed to heat cap 16. Preferably, heating element 12 comprises resistance heating elements and temperature sensors that permit programmed controlled of the temperature of cap 16. Cap 16 is maintained at a temperature above the condensation points of the components of the reaction mixture. Generally, cap 16 may be maintained at a temperature in the range of 94–110° C. Preferably, cap 16 is maintained at a temperature in the range of about 102° C. to about 105° C. since the principal solvent in the reaction mixture is usually water. More preferably, cap 16 is maintained at 103° C. Preferably, in embodiments employing thermal cycling, the cap-heating components described above are thermally isolated from heating-conducting component 20 employed to cyclically control the temperature of reaction mixture 22.

Selection of appropriate materials for the components described above is well within the skill of an ordinary mechanical engineer. Exemplary criterion for material selection include (i) degree of thermal expansion, especially for amplification schemes employing thermal cycling, and its affect on the alignment of the optical components, (ii) optical transmission properties in the excitation wavelengths and fluorophore emission wavelengths employed, (iii) chemical inertness of the reaction chamber relative to components of the reaction mixture, (iv) degree to which critical reaction components, e.g. polymerases, target nucleic acids, would tend to adsorb onto chamber walls, (v) minimization of fluorescent materials in the optical pathway, and the like. Typically, tubes containing amplification reaction mixtures are made of polypropylene or like materials.

Figure 2:
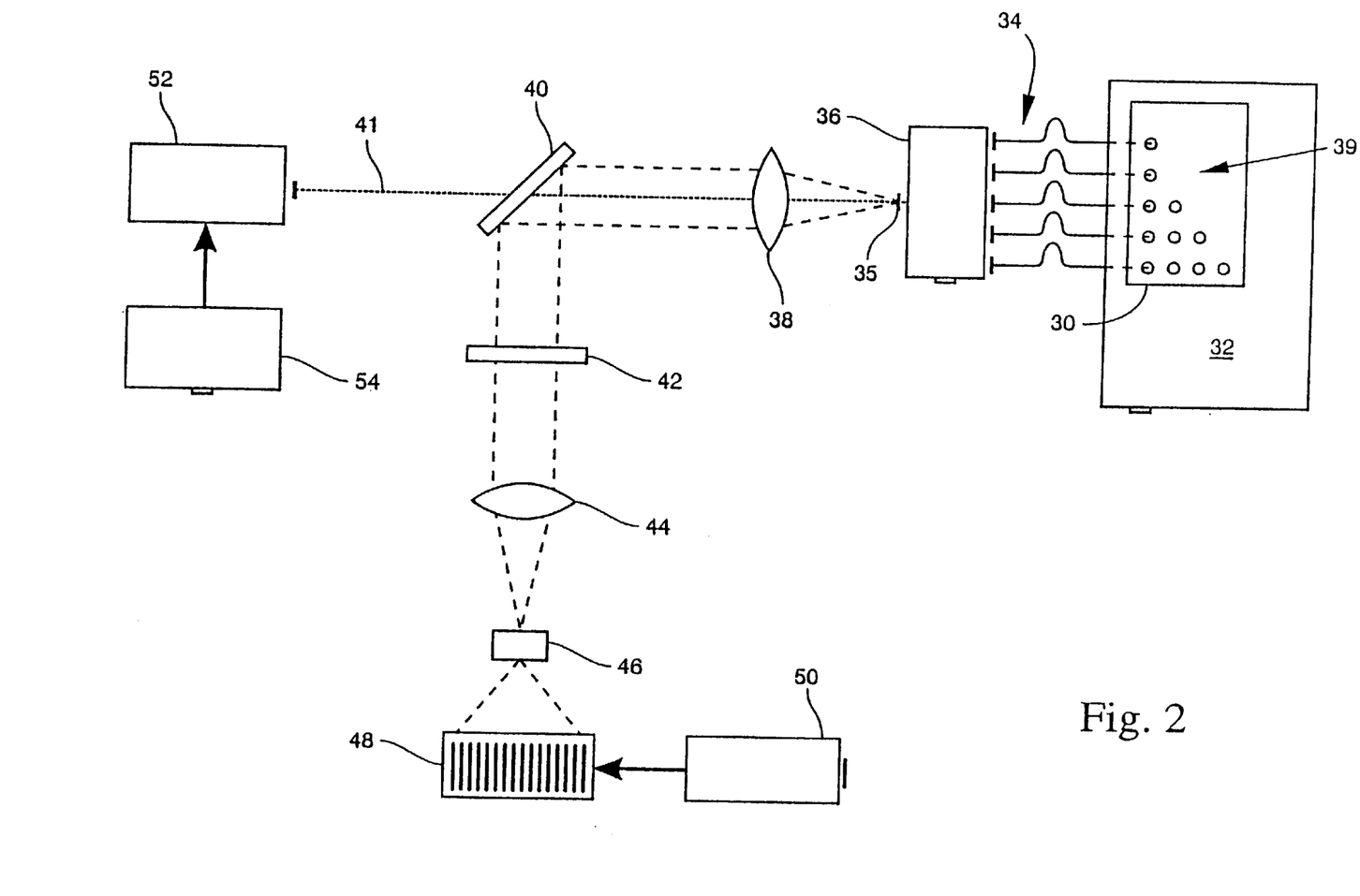
FIG. 2 diagrammatically illustrates a preferred embodiment for simultaneously monitoring a plurality of amplification reactions by sequentially interrogating reactions via a fiber optic multiplexer.

The sample interface shown in FIG. 1 may be employed individually or it may be employed as one of a plurality of identical interfaces in a single instrument, as shown diagrammatically in FIG. 2. In the illustrated embodiment, individual sample interfaces 31, arrayed in holder 30 (which may, for example, be a heating block associated with thermal cycler 32, such as described in Mossa et al, European patent application No. 91311090.4, publ. No. 0488769 A2) are connected by fiber optics 34 to fiber optic multiplexer 36, which selectively permits transmission between individual fiber optics and port 35, e.g under user control via a programmed microprocessor. In a preferred configuration, excitation beam 41, generated by light source 52 and controller 54, passes through beam splitter 40 and is focused onto port 35 by lens 38, where it is sequentially directed by fiber optic multiplexer 36 to each of a predetermined set, or subset, of fiber optics 34. Conversely, a fluorescent signal generated in a reaction chambers is collected by lens 8 and focused onto a fiber optic which, in turn, transmits the signal to a detection and analysis means, possibly via a fiber optic multiplexer. Returning to FIG. 2, a fluorescent signal collected by a sample interface is directed to fiber optic multiplexer 36 where it emerges through port 35 and is collected and collimated by lens 38. Lens 38 directs the fluorescent signal to beam splitter 40 which, in turn, selectively directs the signal through cut-off filter 42, which prevents light from the excitation beam from reaching the signal detection components. Beam splitter 40 may be a conventional dichroic mirror, a fully reflective mirror with an aperture to pass the excitation beam (e.g. as disclosed in U.S. Pat. No. 4,577,109), or like component. After passing through cut-off filter 42, the fluorescent signal is directed by lens 44 to a spectral analyzer which spectrally separates the fluorescent signal and measures the intensities of a plurality of the spectral components of the signal. Typically, a spectral analyzer comprises means for separating the fluorescent signal into its spectral components, such as a prism, diffraction grating, or the like, and an array of photo-detectors, such as a diode array, a charge-coupled device (CCD) system, an array of bandpass filters and photomultiplier tubes, or the like. In the preferred embodiment of FIG. 2, the spectral analyzer comprises diffraction grating 46 (e.g., model CP-140, Jobin-Yvon, NJ) and CCD array 48 (e.g., model S2135 Princeton Instruments, NJ), which is linked to CCD controller 50.

An exemplary CCD array suitable for analyzing fluorescent signal from fluorescein and tetramethylrhodamine is partitioned into 21 collection bins which span the 500 nm to 650 nm region of the spectrum. Each bin collects light over a 8.5 nm window. Clearly, many alternative configurations may also be employed. An exemplary application of a CCD array for spectral analysis is described in Karger et al, Nucleic Acids Research, 19: 4955–4962 (1991).

Analyzing the fluorescent signal based on data collected by a spectral analyzer is desirable since components of the signal due to one or more first fluorescent indicators and a second fluorescent indicator (from which intensity ratios are calculated) can be analyzed simultaneously and without the introduction of wavelength-specific system variability that might arise, e.g. by misalignment, in a system based on multiple beam splitters, filters, and photomultiplier tubes. Also, a spectral analyzer permits the use of "virtual filters" or the programmed manipulation of data generated from the array of photo-detectors, wherein a plurality of discrete wavelength ranges are sampled—in analogy with physical bandpass filters—under programmable control via an associated microprocessor. This capability permits a high degree of flexibility in the selection of dyes as first and second fluorescent indicators.

Generally, the detection and analysis means may be any detection apparatus to provides a readout that reflect the ratio of intensities of the signals generated by the first and second fluorescent indicators. Such apparatus is well know in the art, as exemplified by U.S. Pat. Nos. 4,577,109 and 4,786,886 and references such as The Photonics Design & Applications Handbook, 39th Edition (Laurin Publishing Co., Pittsfield, Mass., 1993).

Preferably, the system of the invention is employed to monitor PCRs, although it may also be employed with a variety of other amplification schemes, such as LCR. Descriptions of and guidance for conducting PCRs is provided in an extensive literature on the subject, e.g. including Innis et al (cited above) and McPherson et al (cited above). Briefly, in a PCR two oligonucleotides are used as primers for a series of synthetic reactions that are catalyzed by a DNA polymerase. These oligonucleotides typically have different sequences and are complementary to sequences that (i) lie on opposite strands of the template, or target, DNA and (ii) flank the segment of DNA that is to be amplified. The target DNA is first denatured by heating in the presence of a large molar excess of each of the two oligonucleotides and the four deoxynucleoside triphosphates (dNTPs). The reaction mixture is then cooled to a temperature that allows the oligonucleotide primers to anneal to their target sequences, after which the annealed primers are extended with DNA polymerase. The cycle of denaturation, annealing, and extension is then repeated many times, typically 25–35 times. Because the products of one round of amplification serve as target nucleic acids for the next, each successive cycle essentially doubles the amount of target DNA, or amplification product.

As mentioned above an important aspect of the invention is the fluorescent dyes used as the first and second fluorescent indicators. By examining the ratio of the fluorescent intensities of the indicators, the effects of most sources of systematic variability, which would be apparent in the intensities alone, are eliminated. Generally, in accordance with the invention, the first fluorescent indicator may be a complex-forming dye or a dye covalently attached to an oligonucleotide probe which is degraded during polymerization steps to generate a signal. This later embodiment relates to the so-called "Tacman" approach, described by Holland et al, Proc. Natl. Acad. Sci., 88: 7276–7280 (1991). As used herein, the term "complex-forming" in reference to a dye means that a dye is capable of forming a stable non-covalent complex with either double stranded or triple stranded nucleic acid structures, usually DNA, and that the dye's fluorescent characteristics are substantially different in the complexed state as compared to a non-complexed, i.e. usually free-solution, state. Preferably, the quantum efficiency of fluorescence of an complex-forming dye is enhanced in the complexed state as compared to the free-solution state, thereby resulting in enhanced fluorescent upon complex formation. Exemplary complex-forming dyes include ethidium bromide, propidium iodide, thiazole orange, acridine orange, daunomycin, mepacrine, 4',6'-diaminidino-2-phenylindole (DAPI), oxazole orange, bis-benzimidaxole dyes, such as Hoechst 33258 and Hoechst 33342, and heterodimers of various intercalating dyes, such as ethidium, acridine, thiazolium, and oxazolium dyes (known by their acronyms POPRO, BOPRO, YOPRO, and TOPRO), and like dyes, which are described in the following references: Haugland, pgs. 221–229 in Handbook of Fluorescent Probes and Research Chemicals, 5th Edition (Molecular Probes, Inc., Eugene, 1992); Glazer et al, Proc. Natl. Acad. Sci., 87: 3851–3855 (1990); Srinivasan et al, Applied and Theoretical Electrophoresis, 3: 235–239 (1993); Kapuscinski et al, Anal. Biochem., 83: 252–257 (1977); Hill, Anal. Biochem., 70: 635–638 (1976); Setaro et al, Anal. Biochem., 71: 313–317 (1976); and Latt et al, J. Histochem. Cytochem., 24:24–33 (1976); and Rye et al, Nucleic Acids Research, 20: 2803–2812 (1992). Preferably, when complex-forming dyes are employed as first fluorescent indicators, such dyes are selected from the group consisting of thiazole orange, ethidium bromide, and TOPRO.

Dyes employed as second fluorescent indicators include fluorescent dyes whose fluorescent characteristics are substantially unaffected by the presence or association with nucleic acids, particularly double stranded DNA. Such dyes may include virtually any fluorescent dye fulfilling this criterion which is also spectrally resolvable from whatever first fluorescent indicators that are employed. Preferred second fluorescent indicators include rhodamine dyes and fluorescein dyes. More preferably, the second fluorescent indicator is tetramethylrhodamine or 2',4',5',7',-tetrachloro-4,7-dichlorofluorescein, the latter being disclosed by Menchen et al, U.S. Pat. No. 5,188,934.

In a preferred embodiment, a first fluorescent indicator and a second fluorescent indicator are both covalently attached to an oligonucleotide probe as described by Lee et al, Nucleic Acid Research, 21: 3761–3766 (1993). More specifically, fluorescein is used as the first fluorescent indicator and tetramethylrhodamine is used as the second fluorescent indicator such that the tetramethylrhodamine moiety substantially quenches any fluorescent emissions by the fluorescein moiety. Thus, when both dyes are attached to the same oligonucleotide, only the tetramethylrhodamine is capable of generating a fluorescent signal. When the oligonucleotide is cleaved, e.g. via the 5'→3' exonuclease activity of a DNA polymerase, separating the two dyes, the fluorescein become capable of generating a fluorescent signal. Preferably, in this embodiment, the excitation beam is generated from the 488 nm emission line of an argon ion laser. In accordance with the invention, in a PCR the production of "free" fluorescein in this embodiment is proportional to the amount of DNA synthesis catalyzed by the DNA polymerase employed, and hence, the amount of amplification product. In this embodiment, preferably the first fluorescent indicator is fluorescein, e.g. 6-FAM (available from Applied Biosystems, Foster City), and the second fluorescent indicator is either tetramethylrhodamine or 2',4',5',7',-tetrachloro-4,7-dichlorofluorescein.

Such oligonucleotide probes of the invention can be synthesized by a number of approaches, e.g. Ozaki et al, Nucleic Acids Research, 20: 5205–5214 (1992); Agrawal et al, Nucleic Acids Research, 18: 5419–5423 (1990); or the like. Preferably, the oligonucleotide probes are synthesized on an automated solid phase DNA synthesizer using phosphoramidite chemistry, e.g. Applied Biosystems, Inc. model 392 or 394 DNA synthesizer (Foster City, Calif.). The first and second fluorescent indicators can be covalently attached to predetermined nucleotide of an oligonucleotide by using nucleoside phosphoramidite monomers containing reactive groups. For example, such reactive groups can be on a phosphate, or phosphate analog, e.g. Agrawal et al (cited above), on the 5' hydroxyl when attachment is to the 5' terminal nucleotide, e.g. Fung et al, U.S. Pat. No. 4,757,141 or Hobbs Jr., U.S. Pat. No. 4,997,928, and on base moieties, e.g. as disclosed by Ruth, U.S. Pat. No. 4,948,882; Haralambidis et al, Nucleic Acids Research, 15: 4857–4876 (1987); Urdea et al, U.S. Pat. No. 5,093,232; Cruickshank U.S. Pat. No. 5,091,519; Hobbs Jr. et al, U.S. Pat. No. 5,151,507; or the like. Most preferably, nucleotides having pyrimidine moieties are derivatized. In further preference, the 3' terminal nucleotide of the oligonucleotide probe is blocked or rendered incapable of extension by a nucleic acid polymerase. Such blocking is conveniently carried out by the attachment of a phosphate group, e.g. via reagents described by Horn and Urdea, Tetrahedron Lett., 27: 4705 (1986), and commercially available as 5' Phosphate-ON™ from Clontech Laboratories (Palo Alto, Calif.). Preferably, the oligonucleotide probe is in the range of 15–60 nucleotides in length. More preferably, the oligonucleotide probe is in the range of 18–30 nucleotides in length.

The separation of the first and second fluorescent indicators within the oligonucleotide probe can vary depending on the nature of the first fluorescent indicator and second fluorescent indicator, the manner in which they are attached, the illumination source, and the like. Guidance concerning the selection of an appropriate distance for a given embodiment is found in numerous references on resonant energy transfer between fluorescent molecules and quenching molecules (also sometimes referred to as "donor" molecules and "acceptor" molecules, respectively), e.g. Stryer and Haugland, Proc. Natl. Acad. Sci., 58: 719–726 (1967); Clegg Meth. Enzymol., 211: 353–388 (1992); Cardullo et al, Proc. Natl. Acad. Sci., 85: 8790–8794 (1988); Ozaki et al (cited above); Haugland (cited above); Heller et al, Fed. Proc., 46: 1968 (1987); and the like. The first and second fluorescent indicators must be close enough so that substantially all, e.g. 90%, of the fluorescence from the first fluorescent indicator is quenched. Typically, for energy transfer-based quenching, the distance between the first and second fluorescent indicators should be within the range of 10–100 angstroms. Preferably, the first and second fluorescent indicators are separated by between about 4 to 10 nucleotides, and more preferably, they are separated by between 4 and 6 nucleotides, with the proviso that there are no intervening secondary structures, such as hairpins, or the like. Preferably, either the first or second fluorescent indicator is attached to the 5' terminal nucleotide of the oligonucleotide probe.

Clearly, related embodiments of the above may be employed wherein the first fluorescent indicator is attached to an oligonucleotide probe with another non-fluorescent quenching molecule, instead of a second fluorescent indicator. In such embodiments, the second fluorescent indicator could be virtually any spectrally resolvable fluorescent dye that did not interact with the amplification products.

EXPERIMENTAL

Real Time Monitoring of PCR Amplification of DNA Encoding β-actin from Various Starting Concentrations of Target DNA A 296 basepair segment of a target DNA encoding human β-actin was amplified by PCR from various starting amounts in the range of $5 \times 10^3$ to $1 \times 10^6$ copies of target DNA. The following primers and probe were employed:

| | |
|---|---|
| 5'-TCACCCACACTGTGCCCATCTACGA (forward primer) | (SEQ. I.D. NO.: 1) |
| 5'-CAGCGGAACCGCTCATTGCCAATGGT (reverse primer) | (SEQ. I.D. NO.: 2) |
| 5'-A(FAM)TGCCCT(TMR)CCCCCATGCCATCCTGCGT (probe) | (SEQ. I.D. NO.: 3) | wherein "FAM" indicates a fluorescein molecule coupled to the oligonucleotide by reacting an NHS-ester group attached to the fluorescein's 6 carbon with a 5'-aminophosphate attached to the 5'-terminal deoxyadenosine of the oligonucleotide in accordance with Fung et al, U.S. Pat. No. 5,212,304; and wherein "TMR" indicates a tetramethylrhodamine molecule coupled to the base moiety of the adjacent thymidine via the amino linking agent disclosed by Urdea et al, U.S. Pat. No. 5,093,232.

PCRs were carried out in 0.2 mL MicroAmp tubes (Perkin-Elmer, Norwalk, Conn.) with the following components: 10 mM Tris-HCl, pH 8.3, 50 mM KCl, 3.5 mM MgCl$_2$, 200 µM each of the nucleoside triphosphates (with dUTP substituted for dTTP in accordance with U.S. Pat. No. 5,035,996 to prevent carryover contamination), 300 nM each of forward and reverse primers, AmpliTaq (Perkin-Elmer, Norwalk, Conn.) at 0.05 U/µL. To this mixture was added 5 µL Raji DNA (Applied Biosystems, Foster City, Calif.) at 10 ng/µL, 5 µL probe at 2 µM, and 1 µL uracil N-glycosylase at 1 unit/µL to bring the reaction volume to 51 µL. Heating and cooling cycles were carried out in a model 9600 Thermal Cycler (Perkin-Elmer, Norwalk, Conn.) fitted with a sample holder cover containing the sample interface components of the invention. The following temperature profile was employed: hold for 2 minutes at 50° C.; hold for 10 minutes at 95° C.; cycle through the following temperatures 40 times: 92° C. for 15 seconds, 54° C. for 15 seconds, 72° C. for 1 minute; then hold at 72° C.

Figure 3:
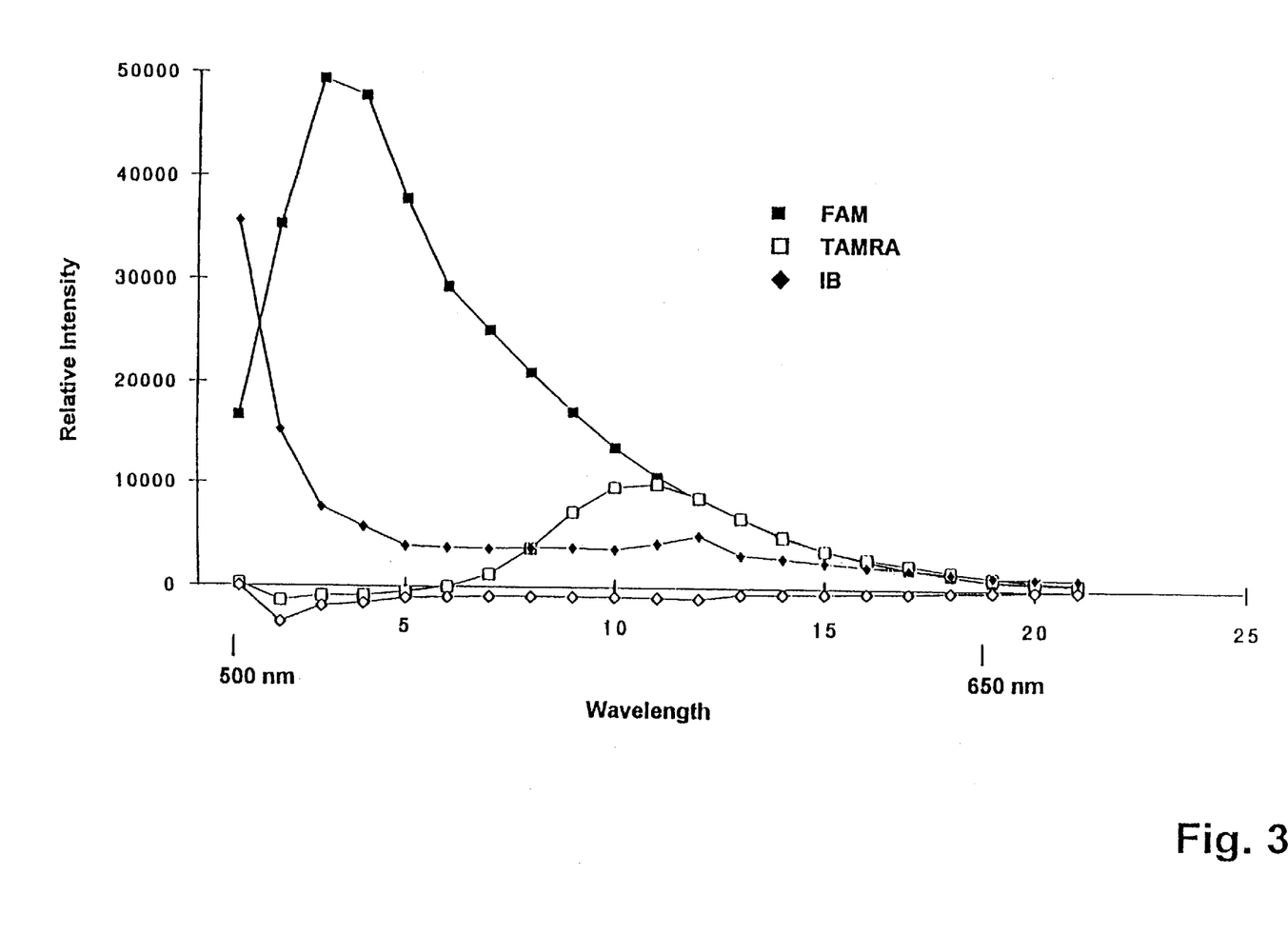
FIG. 3 shows spectrally separated fluorescent intensity data for a tetramethylrhodamine fluorescent indicator, a fluorescein fluorescent indicator, and instrument background registered by a CCD array of the preferred embodiment described below.

FIG. 3 illustrates data showing the emission spectra of the fluorescein and tetramethylrhodamine dyes employed as indicators above and fluorescence due to extraneous sources in the system.

Figure 4:
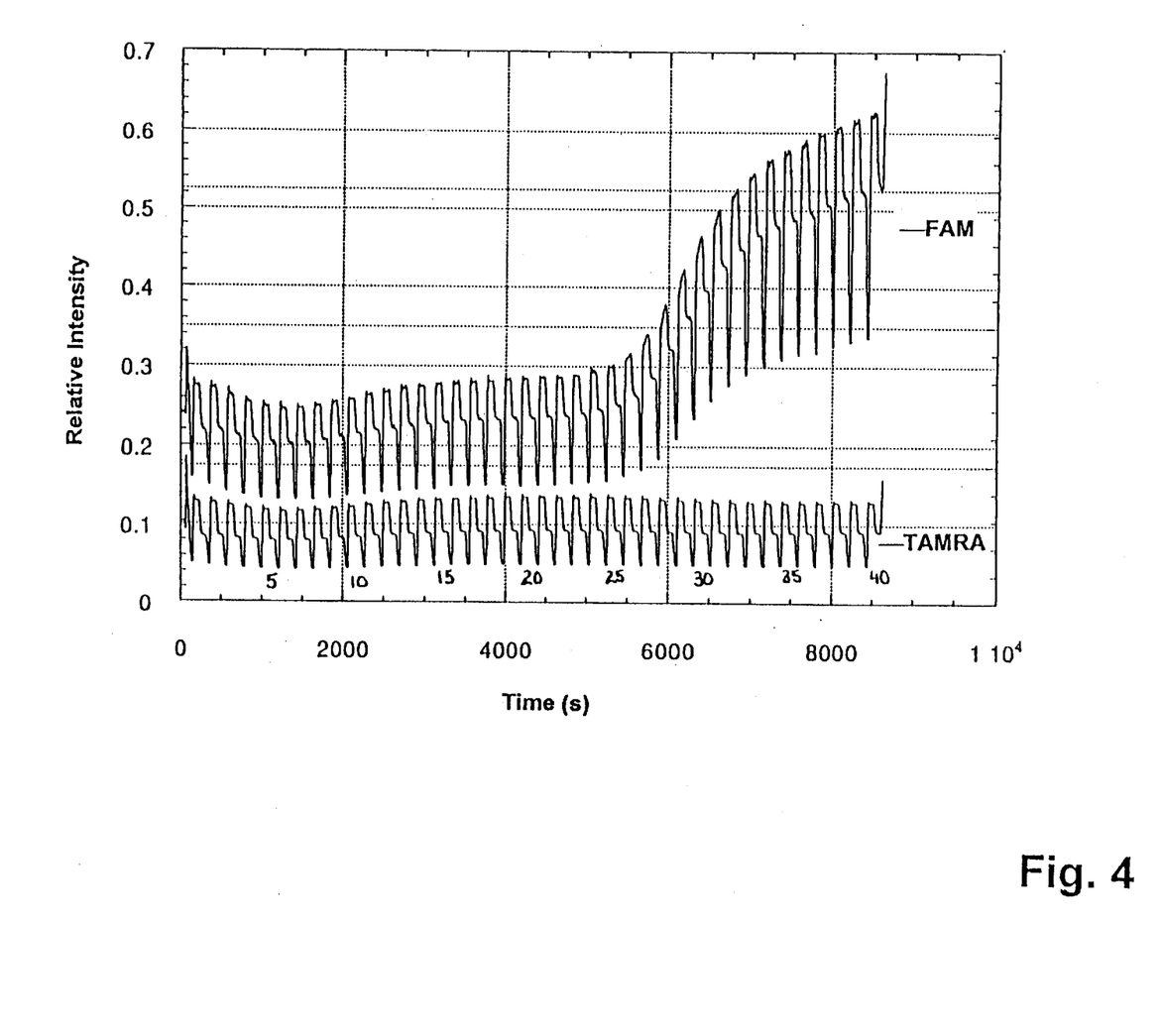
FIG. 4 shows the time dependence of fluorescent signals from a fluorescein dye proportional to the amplification product (first fluorescent indicator) and a tetramethylrhodamine dye employed as a second fluorescent indicator during a typical PCR.
Figure 5:
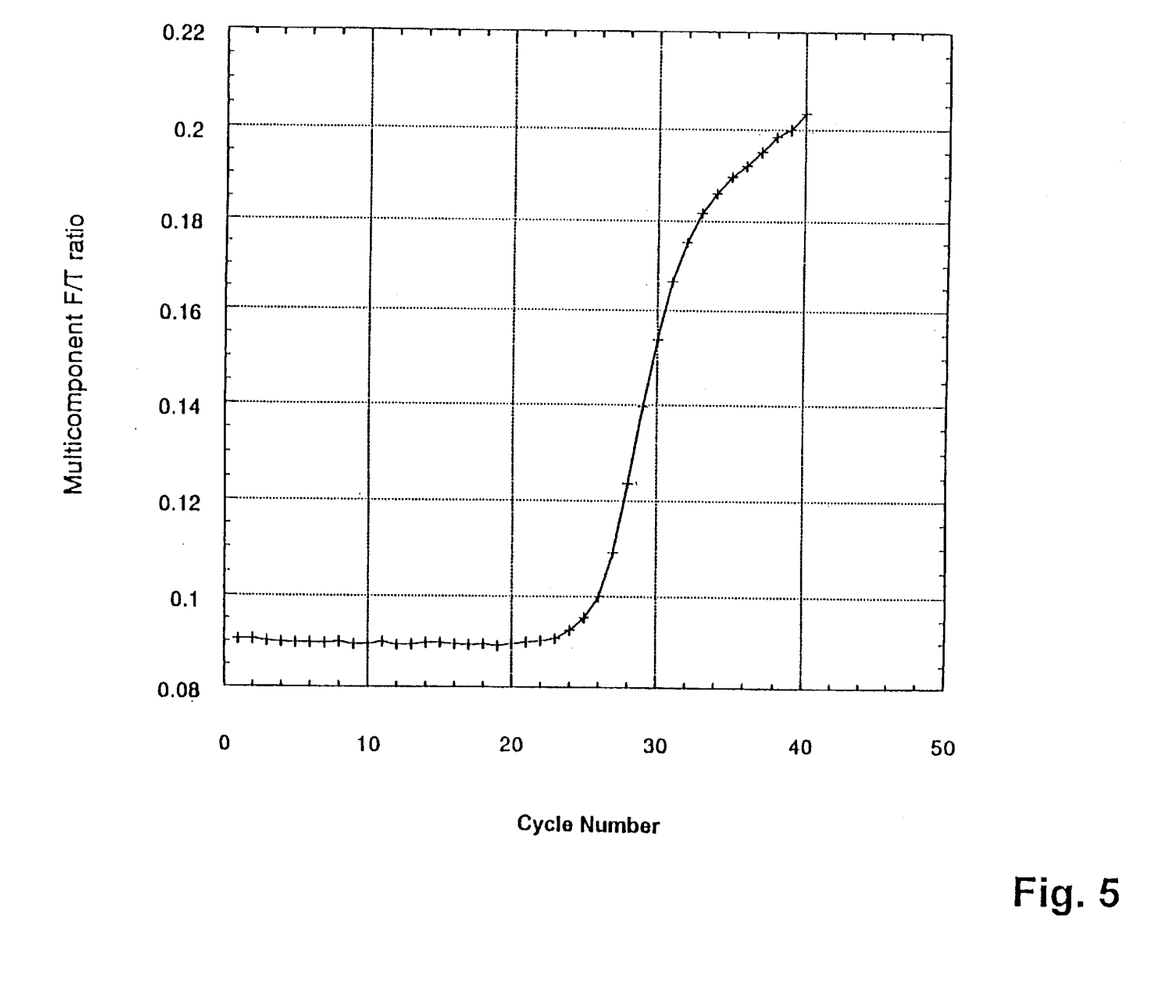
FIG. 5 shows the cycle dependence of the ratio of the intensities of the fluorescein and tetramethylrhodamine dyes from the same PCR whose time dependent data is shown in FIG. 3.

FIG. 4 illustrates data showing fluorescein fluorescent intensity and tetramethylrhodamine fluorescent intensity as a function of cycle number. The high frequency oscillations in intensity reflect the temperature dependence of the fluorescent emission of the two dyes. An increase in base line fluorescence for both dyes between cycles 10 and 28 is a system-based variation. In FIG. 5, which illustrates the ratio of fluorescein-to-tetramethylrhodamine fluorescent intensity from the same data, the system-based variation is eliminated and the RMS of fluctuations in the readout signal, that is, the ratio of fluorescent intensities, is less than 1% of the average magnitude of the measured ratio.

Figure 6:
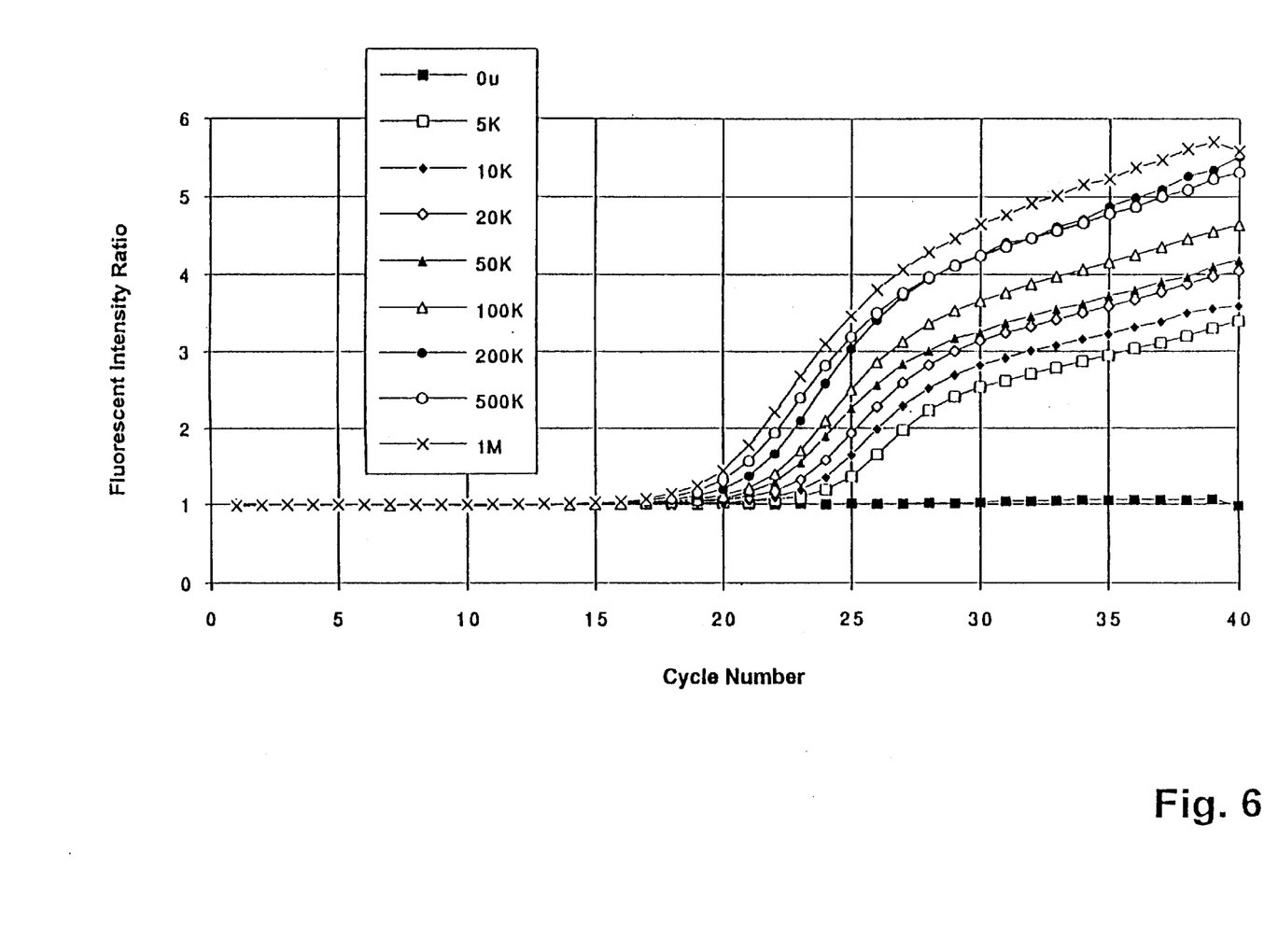
FIG. 6 shows data relating the amount of amplification product to cycle number in separate PCRs having different starting concentrations of the same target nucleic acid.

FIG. 6 illustrates data from PCR of the β-actin DNA starting from amounts ranging from 5000 target molecules to 106 target molecules as indicated in the figure.

What is claimed is:

1. An apparatus comprising:
   a sample holder for holding a sealed reaction chamber, the sealed reaction chamber including a sample, an optical interface and an air gap between the sample and the optical interface;
   a fiber optic cable positioned outside the sealed reaction chamber to deliver an excitation beam to the sample housed within the reaction chamber and to receive light emitted by the sample; and
   a lens co-axially disposed with the fiber optic cable and positioned outside the reaction chamber to focus the excitation beam through the optical interface and the air gap into a volume of the sample and to collect and transmit to the fiber optic cable through the optical interface and the air gap light emitted within the volume of the sample.

2. The apparatus according to claim 1 wherein the lens is not in contact with the reaction chamber.

3. The apparatus according to claim 1 wherein the lens is separated from the reaction chamber by an air gap.

4. The apparatus according to claim 1 wherein the apparatus further includes a mechanism for heating the optical interface to reduce condensation of the sample on the optical interface.

5. The apparatus according to claim 1 wherein the sample holder includes a removable reaction chamber for holding the sample.

6. The apparatus according to claim 1 wherein the lens is positioned above the sample holder.

7. The apparatus according to claim 1 wherein the apparatus further includes a detection and analysis mechanism for receiving first and second fluorescent signals from the fiber optic cable.

8. An apparatus comprising:
   a sealable reaction chamber which includes an optical interface;
   a fiber optic cable positioned outside the sealable reaction chamber to deliver an excitation beam to a sample housed within the reaction chamber and to receive light emitted by the sample; and
   a lens co-axially disposed with the fiber optic cable and positioned outside the reaction chamber to focus the excitation beam through the optical interface into a volume of the sample and to collect and transmit to the fiber optic cable through the optical interface light emitted within the volume of the sample.

9. The apparatus according to claim 8 wherein the lens is not in contact with the reaction chamber.

10. The apparatus according to claim 8 wherein the lens is separated from the reaction chamber by an air gap.

11. The apparatus according to claim 8 wherein the apparatus further includes a mechanism for heating the optical interface to reduce condensation of the sample on the optical interface.

12. The apparatus according to claim 8 wherein the optical interface is positioned on a top of the reaction chamber and the lens is positioned above the optical interface.

13. The apparatus according to claim 8 wherein the reaction chamber is removable from the apparatus.

14. The apparatus according to claim 8 wherein the apparatus further includes a detection and analysis mechanism for receiving first and second fluorescent signals from the fiber optic cable.

15. An apparatus comprising:
- a plurality of sample holders for holding a plurality of sealed reaction chambers, each sealed reaction chamber including a sample, an optical interface and an air gap between the sample and the optical interface;
- a plurality of fiber optic cables positioned outside the sealed reaction chambers to deliver an excitation beam to samples housed within the plurality of reaction chambers and to receive light emitted by the samples; and
- a plurality of lenses co-axially disposed with the fiber optic cables and positioned outside the reaction chambers to focus the excitation beams through the optical interfaces and the air gaps into volumes of the samples and to collect and transmit to the fiber optic cables through the optical interface and the air gap light emitted within the volumes of the samples.

16. The apparatus according to claim 15 wherein the apparatus further includes a fiber optic multiplexer for coupling a detection and analysis mechanism to each of the plurality of fiber optic cables.

17. The apparatus according to claim 15 wherein the plurality of lenses are not in contact with the reaction chambers.

18. The apparatus according to claim 15 wherein the plurality of lenses are separated from the reaction chambers by air gaps.

19. The apparatus according to claim 15 wherein the plurality of lenses are positioned above the sample holders.

20. The apparatus according to claim 15 wherein the apparatus further includes a mechanism for heating the optical interface to reduce condensation of the sample on the optical interface.

21. The apparatus according to claim 15 wherein the plurality of sample holders include one or more removable reaction chambers for holding the sample.

22. The apparatus according to claim 15 wherein the apparatus further includes a detection and analysis mechanism for receiving first and second fluorescent signals from the fiber optic cable.

23. An apparatus comprising:
- a plurality of sealable reaction chambers which each include an optical interface;
- a plurality of fiber optic cables positioned outside the sealable reaction chambers to deliver excitation beams to samples housed within the plurality of reaction chambers and to receive light emitted by the samples; and
- a plurality of lenses co-axially disposed with the fiber optic cables and positioned outside the reaction chambers to focus the excitation beams through the optical interfaces into volumes of samples housed within the plurality of reaction chambers and to collect and transmit to the fiber optic cables through the optical interfaces light emitted within the volumes of the samples.

24. The apparatus according to claim 23 wherein the lenses are not in contact with the reaction chambers.

25. The apparatus according to claim 23 wherein the lenses are separated from the reaction chambers by air gaps.

26. The apparatus according to claim 23 wherein the reaction chambers are removable from the apparatus.

27. The apparatus according to claim 23 wherein the lenses are positioned above the sample holders.

28. A method for monitoring the formation of a nucleic acid amplification reaction product comprising:
- amplifying a nucleic acid sequence in a sample in a sealed reaction chamber which includes an optical interface and an air gap between the sample and the optical interface;
- delivering an excitation beam from a fiber optic cable positioned outside the sealed reaction chamber into a volume of the sample through the optical interface and the air gap; and
- collecting light emitted by the volume of sample within the fiber optic cable through the optical interface and the air gap.

29. The method according to claim 28 wherein delivering and collecting including passing the excitation beam and light through a lens which is positioned outside the sealed reaction chamber between the fiber optic cable and the reaction chamber.

30. The method according to claim 29 wherein the lens is not in contact with the reaction chamber.

31. The method according to claim 28 wherein delivering and collecting is performed above the reaction chamber.

32. The method according to claim 28 further including the step of heating the optical interface to reduce condensation of the sample on the optical interface.

* * * * *